(12) United States Patent
Olsson et al.

(10) Patent No.: US 10,993,844 B2
(45) Date of Patent: May 4, 2021

(54) ABSORBENT ARTICLE AND METHOD FOR MANUFACTURING AN ABSORBENT ARTICLE

(71) Applicant: Essity Hygiene and Health Aktiebolag, Gothenburg (SE)

(72) Inventors: Anna Klinte Olsson, Gothenburg (SE); Stina Lindlöf, Gothenburg (SE); Lucas Bäck, Gothenburg (SE); Katarina Eriksson, Gothenburg (SE)

(73) Assignee: ESSITY HYGIENE AND HEALTH AKTIEBOLAG, Gothenburg (SE)

( * ) Notice: Subject to any disclaimer, the term of this patent is extended or adjusted under 35 U.S.C. 154(b) by 0 days.

(21) Appl. No.: 16/462,974

(22) PCT Filed: Nov. 23, 2016

(86) PCT No.: PCT/SE2016/051156
§ 371 (c)(1),
(2) Date: May 22, 2019

(87) PCT Pub. No.: WO2018/097771
PCT Pub. Date: May 31, 2018

(65) Prior Publication Data
US 2019/0374390 A1     Dec. 12, 2019

(51) Int. Cl.
*A61F 13/15*     (2006.01)
*A61F 13/49*     (2006.01)
(Continued)

(52) U.S. Cl.
CPC .. *A61F 13/15593* (2013.01); *A61F 13/15747* (2013.01); *A61F 13/49011* (2013.01);
(Continued)

(58) Field of Classification Search
CPC .... A61F 13/4942; A61F 13/19; A61F 13/496; A61F 13/49001; A61F 13/476;
(Continued)

(56) References Cited

U.S. PATENT DOCUMENTS 5,674,213 A * 10/1997 Sauer .................. A61F 13/4942
604/385.01
5,706,524 A *  1/1998 Herrin ..................... A61F 13/64
2/311

(Continued)

FOREIGN PATENT DOCUMENTS

| CN | 101795650 A | 8/2010 |
| CN | 101909568 A | 12/2010 |

(Continued)

OTHER PUBLICATIONS

International Search Report and Written Opinion for International Application No. PCT/SE2016/051156, dated Jun. 13, 2017—13 pages.

(Continued)

*Primary Examiner* — Jacqueline F Stephens
(74) *Attorney, Agent, or Firm* — Buchanan Ingersoll & Rooney P.C.

(57) ABSTRACT

An absorbent article having a longitudinal direction, a transverse direction and a thickness direction and comprising a topsheet, a backsheet and an absorbent core is disclosed. The article has, in the longitudinal direction, a front portion, a back portion, and a crotch portion located between the front and rear portions. The front and back portions define a waist edge and a leg edge, and the crotch portion defines two crotch edges. A first elastic element extends along the waist edge, a second elastic element extends along the leg edge and a third and a fourth elastic element each extend along one of the crotch edges. The topsheet or the bottomsheet or another sheet is folded along the waist edge, (Continued)

leg edge and crotch edges so as to enclose at least a part of each corresponding elastic element.

21 Claims, 4 Drawing Sheets

(51) Int. Cl.
A61F 13/513 (2006.01)
A61F 13/514 (2006.01)
A61F 13/53 (2006.01)

(52) U.S. Cl.
CPC ...... *A61F 13/49017* (2013.01); *A61F 13/513* (2013.01); *A61F 13/51456* (2013.01); *A61F 13/53* (2013.01); *A61F 2013/49074* (2013.01)

(58) Field of Classification Search
CPC ............ A61F 13/15; A61F 2013/49038; A61F 13/15593; A61F 13/15747; A61F 13/49011; A61F 13/49017; A61F 13/513; A61F 13/51456; A61F 13/53; A61F 2013/49074; A61F 13/49
See application file for complete search history.

(56) References Cited

U.S. PATENT DOCUMENTS

| | | | | | |
|---|---|---|---|---|---|
| 5,827,259 | A | * | 10/1998 | Laux | A61F 13/49011 604/385.29 |
| 6,083,212 | A | * | 7/2000 | Kumasaka | A61F 13/496 604/358 |
| 6,464,677 | B1 | * | 10/2002 | Noguchi | A61F 13/49 604/385.26 |
| 9,028,462 | B2 | * | 5/2015 | Poole | A61F 13/49014 604/385.3 |
| 2007/0066949 | A1 | * | 3/2007 | Magee | A61F 13/495 604/385.01 |
| 2008/0134487 | A1 | * | 6/2008 | Hartono | A61F 13/49011 29/428 |
| 2011/0066127 | A1 | * | 3/2011 | Kuwano | A61F 13/53 604/385.3 |
| 2011/0094661 | A1 | | 4/2011 | Thorson | |
| 2011/0125122 | A1 | | 5/2011 | Thorson et al. | |
| 2012/0323204 | A1 | | 12/2012 | Poole et al. | |
| 2013/0110070 | A1 | | 5/2013 | Nakaoka et al. | |
| 2014/0288521 | A1 | | 9/2014 | Wade et al. | |
| 2016/0220425 | A1 | | 8/2016 | Zink et al. | |

FOREIGN PATENT DOCUMENTS

| | | |
|---|---|---|
| CN | 105434113 A | 3/2016 |
| CN | 105997360 A | 10/2016 |
| EP | 0865780 A2 | 9/1998 |
| EP | 1537842 A2 | 6/2005 |
| EP | 2 275 065 A1 | 1/2011 |
| EP | 2832328 A1 | 2/2015 |
| EP | 3053558 A1 | 8/2016 |
| JP | H10258082 A | 9/1998 |
| JP | 2002159529 A | 6/2002 |
| JP | 2009160129 A | 7/2009 |
| JP | 2009240639 A | 10/2009 |
| JP | 2010511462 A | 4/2010 |
| JP | 2012019913 A | 2/2012 |
| JP | 2015202226 A | 11/2015 |
| JP | 201679041 A | 10/2016 |
| WO | 2009/084643 A1 | 7/2009 |
| WO | 2012172446 A2 | 12/2012 |
| WO | 2013153756 A1 | 10/2013 |
| WO | 2015/137127 A1 | 9/2015 |
| WO | 2016099362 A1 | 6/2016 |
| WO | 2016/152784 A1 | 9/2016 |

OTHER PUBLICATIONS

Extended European Search Report dated May 19, 2020, issued by the European Patent Office in corresponding European Application No. 16922179.3-1102, (6 pages).
Office Action (Reason(s)) dated Jul. 13, 2020 by the Japanese Patent Office in corresponding Japanese Patent Application No. 2019-527515, and an English Translation of the Office Action. (9 pages).
Office Action (Notification of the First Office Action) dated Jan. 11, 2021 by the China National Intellectual Property Administration (CNIPA) of the People's Republic of China in corresponding Chinese Patent Application No. 201680090993.3 and an English Translation of the Office Action. (24 pages).

* cited by examiner

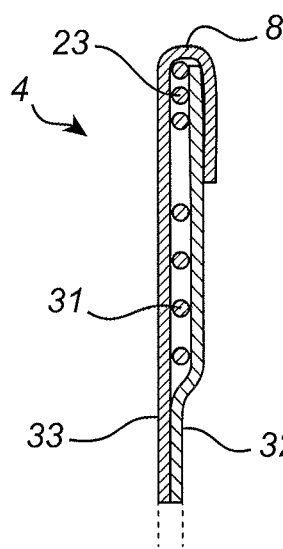 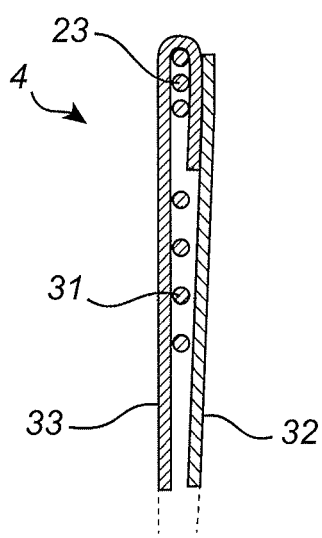 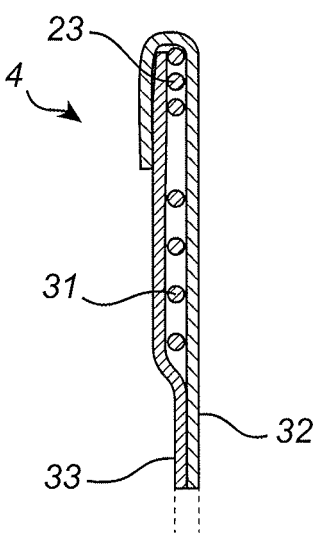
Fig. 4a  Fig. 4b  Fig. 4c
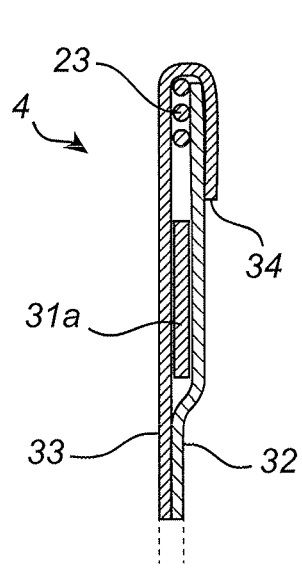 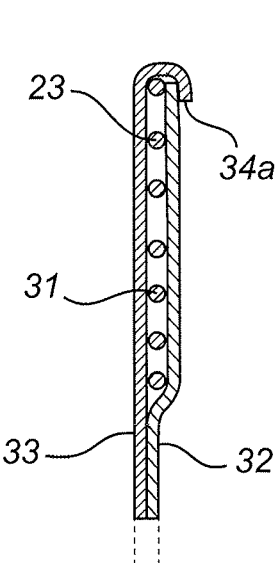 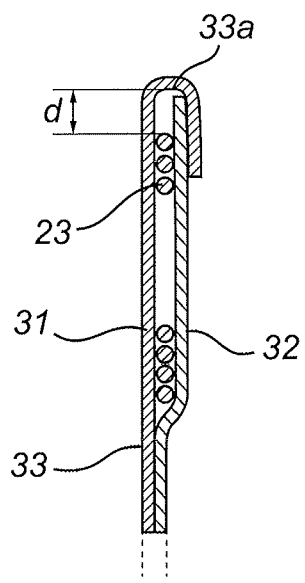
Fig. 4d  Fig. 4e  Fig. 4f
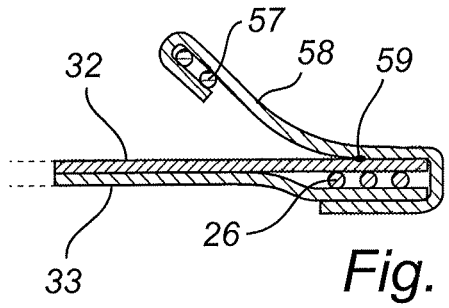
Fig. 5

ABSORBENT ARTICLE AND METHOD FOR MANUFACTURING AN ABSORBENT ARTICLE

CROSS REFERENCE TO RELATED APPLICATIONS

This is a U.S. National Phase application of PCT/SE2016/051156, filed Nov. 23, 2016, the disclosure of which is incorporated herein by reference in its entirety for all purposes.

TECHNICAL FIELD

The invention relates to an absorbent article having a longitudinal direction, a transverse direction and a thickness direction and comprising a topsheet, a backsheet and an absorbent core, and also having, in the longitudinal direction, a front portion, a back portion and a crotch portion between the front portion and the rear portion, wherein the front portion and back portion define a waist edge and a leg edge and the crotch portion defines two crotch edges and wherein a first elastic element extends along the waist edge, a second elastic element extends along the leg edge and a third and a fourth elastic element extend along each one of the crotch edges.

The invention also relates to a method for manufacturing an absorbent article having a longitudinal direction, a transverse direction and a thickness direction. The method comprises: providing a topsheet, a backsheet and an absorbent core; and forming, in the longitudinal direction of the article, a front portion, a back portion and a crotch portion between the front portion and the rear portion, wherein the front portion and back portion define a waist edge and a leg edge and the crotch portion defines two crotch edges. The method also comprises a step of providing a first elastic element extending along the waist edge, a second elastic element extending along the leg edge and a third and a fourth elastic element extending along each one of the crotch edges.

BACKGROUND

Disposable absorbent articles, for example in the form of incontinence liners, baby diapers and sanitary napkins, are well known. The general purpose of such absorbent articles is to absorb, distribute and store various types of body exudates, while providing a high level of comfort and sense of dryness to the wearer during use of the absorbent article. Also, such an absorbent article is configured to prevent the wearer from getting the clothes soiled by such body exudates.

Absorbent articles in the form of incontinence articles are used to protect a wearer against urine leakage. An incontinence article can be configured for example as a pant diaper, a sanitary pant or an incontinence pant adapted for use by a baby, child or adult, male or female user. Also, an incontinence article is designed with an absorption capacity which is adapted to absorb the fluid that is expected to be released into the article when it is worn. Incontinence articles are used to assist persons with incontinence so that they can maintain a normal lifestyle without any inconvenience caused by incontinence.

With regard to adult users of pant-type incontinence articles, there is a particular demand for such articles which are adapted to the male and female anatomy, respectively. Furthermore, there is a demand for incontinence articles which are designed in a manner so that they resemble regular underwear. In fact, adult persons who use incontinence articles may be reluctant to use articles which are "diaper-like" and which are perceived as bulky, uncomfortable and unattractive, and which may be visible if, for example, the user wears tight clothes over an incontinence article.

This means that there is a desire to provide incontinence articles which are less bulky and which have a look and feel which is similar to traditional underwear. Also, there is a desire to provide such incontinence articles which are stylish and attractive for both men and women and which follow the anatomy and body contour of a male and female body. In this manner, a more discreet article can be provided which gives the wearer a higher level of self-confidence, comfort and self-esteem and which provides incontinence protection for users having different lifestyles.

One important factor which contributes to a modern and well-fitting absorbent article such as an incontinence article is the provision of elastic elements along the edges of the article, i.e. along the waist, legs and crotch edges. Such elastic elements are normally provided with a number of elastic threads which are arranged along a waist edge, a leg edge and two crotch edges.

It is furthermore known to seal the waist, leg and crotch edges with a process involving welding, so as to fix the elastic threads along the corresponding edges with the elastic threads between a topsheet and a backsheet. However, according to conventional technology, the elastic threads must be positioned relatively far from the corresponding edges since there are relatively large tolerances involved in the manufacturing process which may cause the threads to end up outside the article during production. This may cause interruptions in the production process, especially if the threads are covered with glue which may cause damage to the production equipment. A manufacturing line for a pant-type absorbent article normally operates at a very high rate and is sensitive to such disturbances. For this reason, the elastic threads must be laid out relatively far from the edges of the article. This means that there will be a large amount of unelasticized web material along the leg and waist edges, which is less attractive and comfortable for the user. Also, such edges make it difficult to give the articles a look similar to regular underwear, which is a further disadvantage.

The patent document WO 2012/172446 discloses a disposable absorbent garment which is arranged to resemble normal cloth underwear. To this end, the garment is provided with an integral waistband comprising two layers having different colours, and including a folded flap which defines an outwardly visible waistband.

Although the article disclosed in WO 2012/172446 is generally intended to solve the above-mentioned problem, there exists a need for further improvements of absorbent articles, in particular incontinence articles, so as to provide such articles with a design which is close to regular underwear while still providing a high level of fit and comfort, in particular regarding the elastic elements provided in the article.

SUMMARY

An object with the present invention is to provide a pant-type absorbent article, and a method for manufacturing thereof, which follow requirements as to fashion, fit and design of male and female underwear and which are adapted to the male and female anatomy. In particular, there is an object to provide elastic elements which contribute to the above requirements.

In accordance with the invention, this object is obtained by means of an absorbent article having a longitudinal direction, a transverse direction and a thickness direction and comprising a topsheet, a backsheet and an absorbent core, and also having, in the longitudinal direction, a front portion, a back portion and a crotch portion between the front portion and the rear portion, wherein the front portion and back portion define a waist edge and a leg edge and the crotch portion defines two crotch edges and wherein a first elastic element extends along the waist edge, a second elastic element extends along the leg edge and a third and a fourth elastic element extend along each one of the crotch edge. One of said sheets or another sheet is folded along said waist edge, leg edge, and crotch edges so as to enclose at least a part of each corresponding elastic element.

The absorbent article according to the invention provides certain advantages due to the fact that the elastic elements can be laid out very close to the above-mentioned edges, which means that the article can be designed in a manner which is close to regular underwear while still providing the desired protection against incontinence and providing sufficient comfort and fit.

According to an embodiment, the article has an elastic element which is sandwiched between an inner side of said backsheet and an inner side of said topsheet, and wherein said backsheet is folded over an outer side of said topsheet. According to a further embodiment, said elastic element is sandwiched between an inner side of said backsheet and an inner side of said topsheet, wherein said topsheet is folded over an outer side of said backsheet.

According to an embodiment, said elastic element is enclosed within a fold defined by said backsheet, wherein said topsheet is attached to said backsheet. According to a further embodiment, said elastic element is enclosed within a fold defined by said topsheet, wherein said topsheet is attached to said backsheet. A distance is defined from the inside of the fold and to the elastic element, said distance being less than 10 mm in an embodiment, preferably less than 5 mm in another embodiment and most preferably less than 3 mm in yet another embodiment.

According to a further embodiment, the crotch portion comprises a web material which is folded over a laminate formed by said topsheet and said backsheet.

The above-mentioned embodiments provide solutions for manufacturing absorbent article according to the invention in a straight-forward and effective manner so as to provide the advantages stated above.

Furthermore, the above-mentioned object of the invention is obtained by means of a method for manufacturing an absorbent article having a longitudinal direction, a transverse direction and a thickness direction. The method comprises: providing a topsheet, a backsheet and an absorbent core; forming, in the longitudinal direction of the article, a front portion, a back portion and a crotch portion between the front portion and the rear portion, wherein the front portion and back portion define a waist edge and a leg edge and the crotch portion defines two crotch edges. The method also comprises a step of providing a first elastic element extending along the waist edge, a second elastic element extending along the leg edge and a third and a fourth elastic element extending along each one of the crotch edges. Furthermore, the method comprises a step of folding said backsheet or said topsheet along said waist edge, leg edge and crotch edges so as to enclose at least a part of each corresponding elastic element.

BRIEF DESCRIPTION OF THE DRAWINGS

The invention will be described in greater detail below with reference to the figures shown in the appended drawings.

FIGS. 4a-4f show cross-sectional views of alternative embodiments of the absorbent article according to the disclosure; and FIG. 5 shows a cross-sectional view of a crotch section of said absorbent article.

DETAILED DESCRIPTION OF PARTICULAR EMBODIMENTS

Different aspects of the present disclosure will be described more fully hereinafter with reference to the enclosed drawings. The embodiments disclosed herein can, however, be realized in many different forms and should not be construed as being limited to the aspects set forth herein.

Figure 1B:
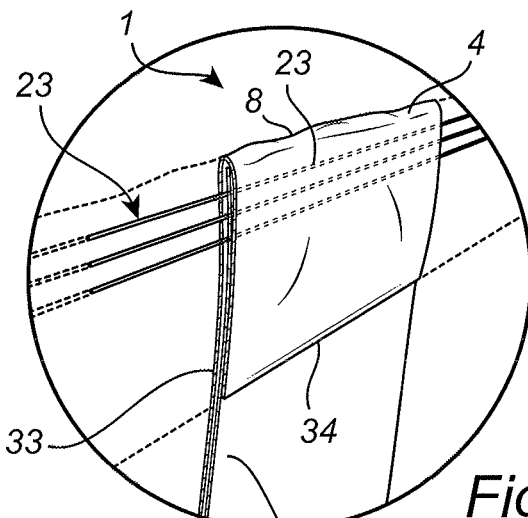
FIG. 1b is a perspective view of an enlarged section of the article of FIG. 1a, in particular showing a part of a waist edge of said absorbent article.
Figure 1A:
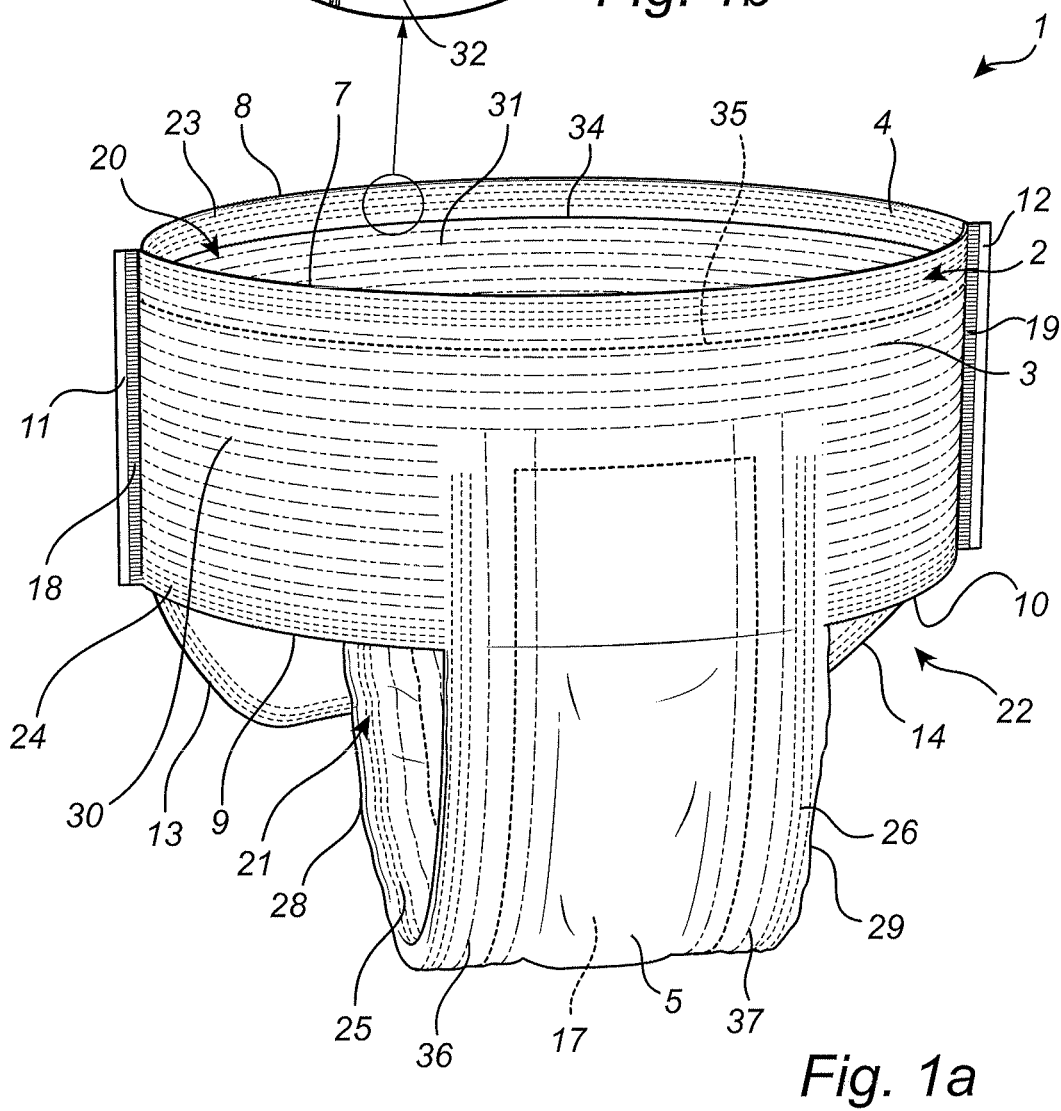
FIG. 1a shows a perspective front view of the absorbent article according to the disclosure.
Figure 2:
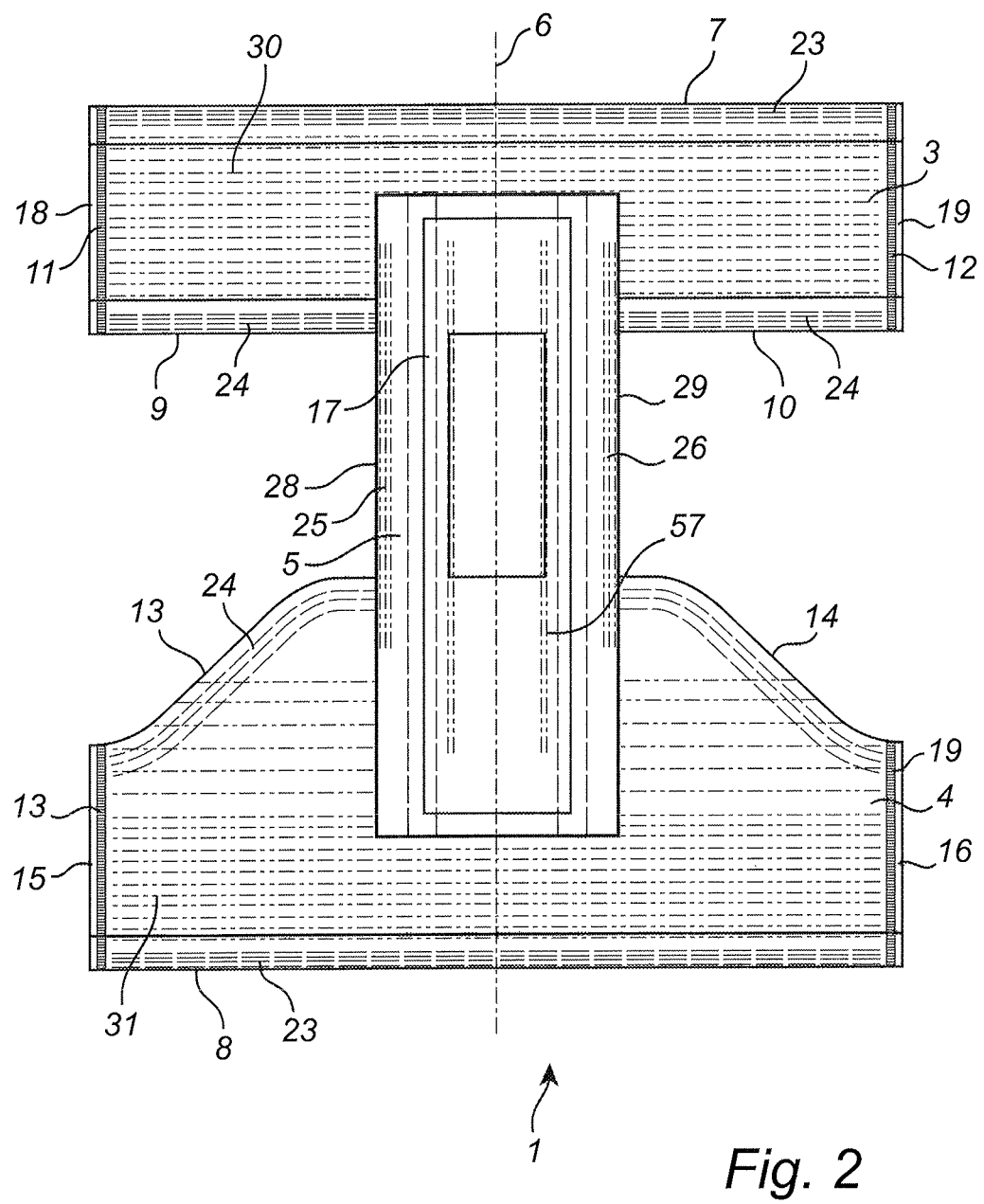
FIG. 2 shows a top view of the absorbent article.

With reference to FIG. 1a of the drawings, there is shown an embodiment of a disposable pant-type absorbent article 1 illustrated in an assembled and ready-to-use state. The same absorbent article 1 is also shown in FIG. 2, but in a condition in which it is laid out flat and as viewed from above in order to show its main components. Furthermore, FIG. 1b is a perspective view of an enlarged section of a part of the absorbent article 1, and will be described in greater detail below.

With reference to FIGS. 1a, 1b and 2, the pant-type absorbent article 1 is for example in the form of a pant diaper, a sanitary pant or an incontinence pant adapted for use by a baby, child or adult, male or female user. The pant-type absorbent article 1 according to FIG. 1 comprises a single-piece chassis 2 having a front portion 3, a back portion 4, a crotch portion 5 connecting the front and back portions 3, 4, and a centre line 6 (see FIG. 2) in the longitudinal direction of the article. The absorbent article 1 has a longitudinal direction, a transverse direction and a thickness direction.

The front portion 3 has a waist edge 7, a pair of leg edges 9, 10 and a pair of side edges 11, 12. Furthermore, the back portion 4 has a waist edge 8, a pair of leg edges 13, 14 and a pair of side edges 15, 16.

As mentioned above, the absorbent article 1 comprises a crotch portion 5, which comprises an absorbent body 17 located mainly in said crotch portion 5. The absorbent body 17 may be manufactured separately from the chassis 2 and inserted and fastened to the chassis 2 at a suitable manufacturing step. This process will be described in greater detail below.

The side edges 11, 12 of the front portion 3 are attached to the opposite side edges 15, 16 of the back portion 4 by means of permanent or re-closable side connections 18, 19 such as side seams, hook and loop fasteners, adhesive fasteners, or the like, in order to at least partly define a waist opening 20 and a pair of leg openings 21, 22.

A first elastic element in the form of an elastic waist component 23 is fastened to the chassis 2 at least partly along the waist edges 7, 8 forming part of the front portion 3 and the back portion 4. The purpose of the elastic waist component 23 is to provide the absorbent article 1 with a good fit around the waist of the user wearing the article. The elastic waist component 23 is fastened relatively close to the waist edges 7, 8, around the waist opening 20.

Furthermore, a second elastic element in the form of an elastic leg component 24 is fastened to the chassis 2 at least partly along the leg edges 9, 10 of the front portion 2 for the purpose of providing the absorbent article 1 with a good fitting around the legs of the user wearing the article. The elastic leg component 24 is fastened relatively close to the leg edges 9, 10.

As shown in particular in FIG. 2, the elastic leg component 24 forms a straight line in the front portion 3 and has a curved configuration in the back portion 4.

Furthermore, a first absorbent body elastic 25 and a second absorbent body elastic 26 are arranged along the crotch portion 5. The first absorbent body elastic 25 is arranged along a first crotch edge 28 whereas the second absorbent body elastic 26 is arranged along a second crotch edge 29. In particular, the first absorbent body elastic 25 and the second absorbent body elastic 26 are arranged relatively close to the longitudinal crotch edges 28, 29. In a similar manner, the elastic waist component 23 and the elastic leg component 24 are also arranged relatively close to the waist edges 7, 8 and the leg edges 9, 10, respectively, as shown in FIG. 1 and FIG. 2.

If the elastic leg component 24 and the elastic waist component 23 are fastened at a location close to the leg and waist edges 7, 8, 9, 10, respectively, less non-elasticised web material is available at the leg and waist edges such that less frills is created along said edges. This is an advantage, since a large amount of material at the leg edges may be perceived as uncomfortable by a user and may give the user an impression that the article is not similar to conventional underwear.

Having the elastic leg feature 24 positioned closer to the leg edge 9, 10 may also result in an absorbent article 1 having an improved fit which corresponds to the shape of the legs of the user. It is thus desirable to provide an elasticised leg edge 9, 10 of the front and back portion 3, 4 that has a more cuff like appearance with less frills, thereby providing the absorbent article 1 with an appearance more similar to cloth underwear.

Furthermore, as shown in FIG. 1a and FIG. 2, the absorbent article 1 comprises a front elastic component 30 and a back elastic component 31 which are both based on a number of elastic threads mounted at a certain distance from each other in a generally parallel manner around the article 1, i.e. the region of the belly and the backside of the user. The purpose of these elastic components 30, 31 is to contribute to a good fit and comfort for the wearer of the article 1. In particular, the configuration of the elastic threads can be adapted to the male and female anatomy and the need for a suitable fit and comfort for male and female users of the article 1.

Furthermore, and as mentioned above, it can be noted that a process of fastening the elastic waist component 23 and the elastic leg component 24 close to an edge of a web material, i.e. in this case close to the waist edges 7, 8 and the leg edges 9, 10, respectively, is difficult due to the manufacturing tolerances of the production line. A production process for a pant-type absorbent article operates at a high rate and such a fully automatized manufacturing line needs to have a certain tolerances. If the elastic threads of the elastic components are positioned too close to the corresponding edges, there is a risk that the threads may actually be laid and positioned outside the edges. Since glue is normally applied to the threads, there is a risk for production interruption if the elastic threads are erroneously positioned outside the actual edges of the article.

Also, as mentioned initially, there is a requirement for producing absorbent articles which are similar to conventional underwear, i.e. having a look and feel corresponding to normal male and female underwear.

For the above-mentioned reasons, and with further reference to FIG. 2 and also FIG. 1b, it is a general principle of the invention that the elastic waist component 23, the elastic leg component 24 and the elastic absorbent body components 25, 26 are fastened by means of a folding arrangement of the article 1 in question. The principles for this folding arrangement are shown in FIG. 1b, which shows an enlargement of a small section of the upper part of the back portion 4, more precisely a section of the absorbent article 1 close to the waist edge 8 of the back portion 4.

In a manner which is conventional as such, the absorbent article 1 comprises a liquid permeable topsheet 32, i.e. a sheet which is intended to face the user of the article 1, and a liquid impermeable backsheet 33, i.e. a sheet which is placed so as to face the garment worn by the user. Generally, the liquid permeable topsheet 32 comprises or consist of a nonwoven material. The topsheet material may further be composed of tow fibres, porous foams, apertured plastic films and similar materials. The materials suited as topsheet materials should be soft and non-irritating to the skin and should be readily penetrated by body fluid, e.g. urine or menstrual fluid, and display low rewetting properties.

Furthermore, the liquid impermeable backsheet 33 may consist of a thin plastic film, e. g. a polyethylene or polypropylene film, a nonwoven material coated with a liquid impervious material, a hydrophobic nonwoven material which resists liquid penetration or laminates of plastic films and nonwoven materials. The backsheet material may be breathable so as to allow vapour to escape from the absorbent article, while still preventing liquids from passing through the backsheet 33 material.

According to various embodiments, the materials which can be used for manufacturing the backsheet 33 include thin and flexible fluid impermeable plastic films, or fluid impermeable nonwoven materials, fluid impermeable foams and fluid impermeable laminates.

Furthermore, the backsheet 33 is formed by a single layer or can alternatively be formed by a multi-layered structure, i.e. a laminate, wherein at least one layer is fluid impermeable. Furthermore, the backsheet 33 can optionally be elastic in either direction. According to further embodiments, the backsheet 33 may be breathable, implying that air and vapor may pass through the backsheet. Furthermore, the backsheet 33 may optionally have an outer, garment-facing surface of a textile material such as nonwoven.

The absorbent core 17 can be formed by a single layer consisting of fibres of cellulosic fluff pulp. According to alternative embodiments, the absorbent core 17 can be made up of any suitable absorbent or fluid-absorbing material as known in the art, for example foam, fiber waddings and similar materials.

Furthermore, the absorbent core 17 may consist of a mixture of cellulosic fluff pulp and a suitable amount of superabsorbent particles. Such superabsorbent material is well known in the field of absorbent articles, and is constituted by a water-swellable and water-insoluble material which is capable of absorbing large quantities of fluid upon formation of a hydrogel. Normal superabsorbent materials are capable of absorbing fluids of at least 10 times its own weight.

According to further embodiments, the absorbent core 17 may further incorporate components for improving the properties of the absorbent core. Some examples of such components are binder fibers, fluid-dispersing materials, fluid acquisition materials, etc. as known in the art. The absorbent core 17 may also be a homogeneous structure or may be a layered structure with laminates of the same or different materials. The absorbent layers may have uniform thickness or may vary in thickness in different parts of the layers.

The topsheet 32 and backsheet 33 may be connected to each other for example by adhesive bonding, gluing or welding by heat or ultrasonic. The topsheet 32 and/or the backsheet 33 may further be attached to the absorbent body by any method known in the art, such as adhesive, heat-bonding etc.

According to an embodiment, the topsheet and backsheet in the parts forming the front portion 3 and the back portion 4 may be of different type than the topsheet and backsheet in the crotch portion 5. In the latter case, it is suitable with a fluid-permeable topsheet and a fluid-impermeable backsheet (as described above) since the absorbent article 1 in an embodiment must have absorbent properties in the crotch portion 5. However, in the parts forming the front portion 3 and the back portion 4, both the topsheet and the backsheet may be for example liquid-impermeable, since these parts of the absorbent article 1 generally do not need to have absorbent properties.

According to the embodiment shown in FIG. 1*b*, the backsheet 33 is configured so that it can be folded along the waist edge 8 of the back portion 4 and over the topsheet 32. In this manner, the elastic waist component 23 is enclosed between the topsheet 32 and the backsheet 33, i.e. so as to cover the elastic waist component 23 by means of the topsheet 32 and the backsheet 33. More precisely, the elastic waist component 23 is positioned between the backsheet 33 and the topsheet 32, and the backsheet 33 is then folded over the topsheet 32. In this manner, an edge 34 of the backsheet 33 is defined along the inside of the absorbent article 1, i.e. facing the user of the article.

The embodiment shown in FIG. 1*b* is configured so that the elastic waist component 23 is fully enclosed by means of the topsheet 32 and the folded backsheet 33. However, according to other embodiments (as will be described below with reference to FIG. 4*e*), the backsheet 33 and the elastic waist component 23 may be dimensioned and configured so that the backsheet 33 is folded in a manner so as to enclose only a part of the elastic waist component 23.

A similar folding process is carried out also as regards the front portion 3, so that the backsheet 33 forms a fold defining an edge 35 (see FIG. 1*a*) along the inside of the absorbent article 1. Furthermore, a similar folding process is carried out also as regards the crotch portion 5, so that a fold is formed with a first edge 36 and a second edge 37 (see FIG. 1*a*) along the absorbent body 17 in the crotch portion 5. Also, a similar folding process is carried out also so as to enclose the elastic leg component 24 along the leg edges 9, 10.

The purpose of the folding procedure as described above is to allow the elastic elements, i.e. the elastic waist component 23, the elastic leg component 24 and the elastic absorbent body components 25, 26, to be positioned very close to the corresponding edge of the absorbent article 1. This means that the absorbent article 1 can be manufactured in a manner with so that it resembles an ordinary undergarment which has an optimized waist elastic function and which is convenient to wear. By positioning the elastic elements very close to each edge of the article, the amount of unelasticized web material which otherwise may occur along the edges can be avoided. In summary, the absorbent article 1 will be more similar in look and feel to regular underwear, while still offering sufficient protection against urine leakage.

In summary, the disclosure is based on the principle that the backsheet 33 or the topsheet 34 is folded along the waist edges 7, 8, leg edges 9, 10 and crotch edges 28, 29 so as to enclose each corresponding elastic element 23, 24, 25, 26 at least partly. Certain alternative embodiments will be further described below.

Figure 3:
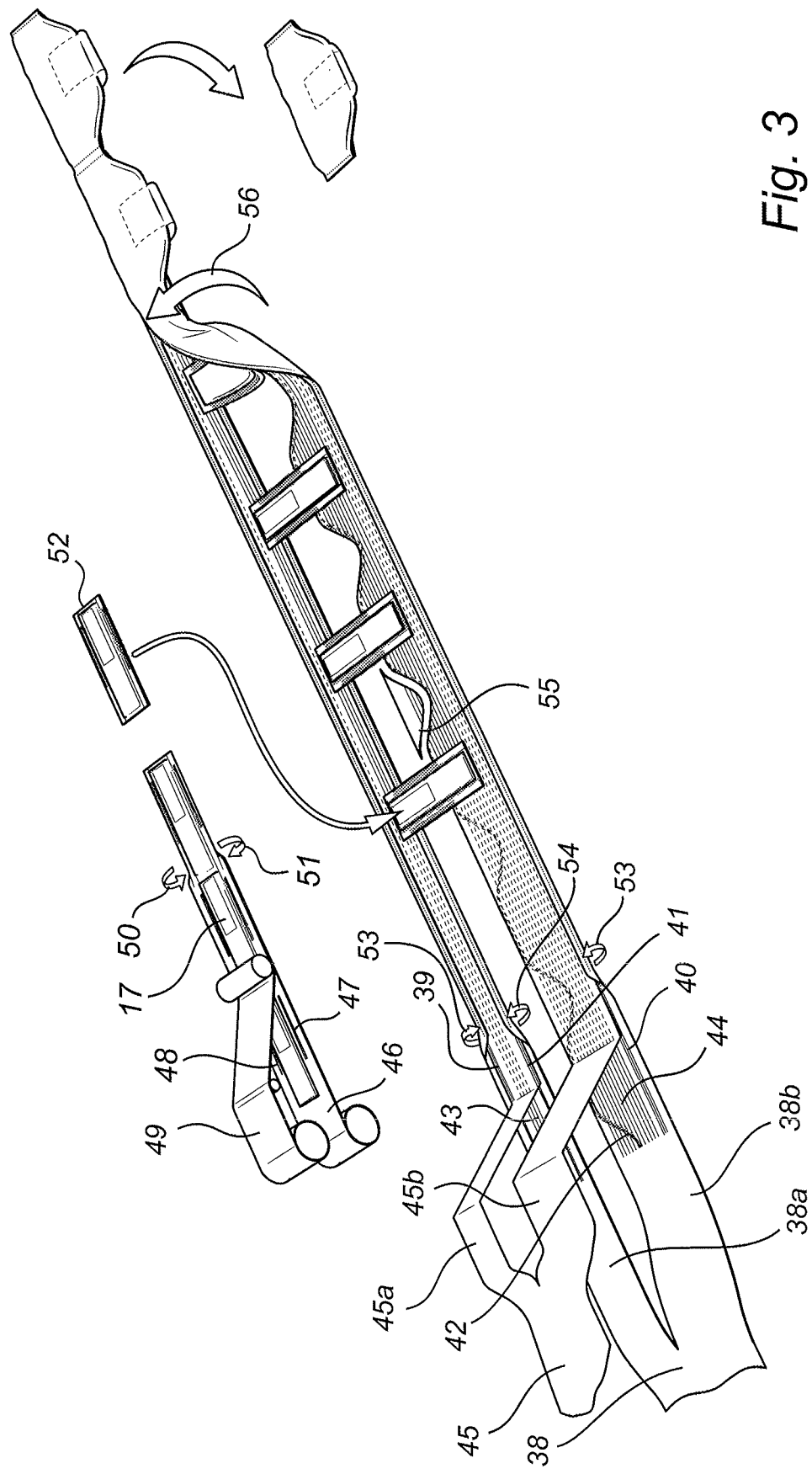
FIG. 3 shows a schematic illustration of a manufacturing process for an absorbent article according to the disclosure.

An example embodiment of a manufacturing line for a pant-type absorbent article 1 is schematically illustrated in FIG. 3. A first continuous sheet 38 of web material is supplied and is also divided, in a lengthwise manner, so as to form a first web section 38*a* and a second web section 38*b*. The first web section 38*a* forms the basis of a backsheet for the front portion 3 (see FIGS. 1*a* and 2) of the absorbent article 1, whereas the second web section 38*b* forms the basis of a backsheet for the back portion 4.

A plurality of strips of elastic material are attached to the first and second web sections 38*a*, 38*b* in a tensioned state. More precisely, a first strip 39 and a second strip 40 of elastic material form the basis of the elastic waist component 23, and a third strip 41 and a fourth strip 42 of elastic material form the basis of the elastic leg component 24. Also, a fifth strip 43 and a sixth strip 44 of elastic material form the basis of the front elastic component 30 and the back elastic component 31, respectively.

The strips 39, 40, 41, 42, 43, 44 of elastic material may be glued or otherwise fastened to the continuous sheets 38*a*, 38*b* of web material, and said strips are intended to form an elastic web feature of the absorbent article 1 as described above with reference to FIGS. 1*a*, 1*b* and 2.

Next, a further continuous sheet 45 of web material is provided and is split longitudinally in order to form a third web section 45*a* and a fourth web section 45*b*. The third web sections 45*a* forms the basis of a topsheet for the front portion 3 whereas the fourth web section 45*b* forms the basis of a topsheet for the back section 4.

The third web section 45*a* and the fourth web section 45*b* are joined to the first web section 38*a* and the second web section 38*b*, respectively, in order to form a laminated product having the strips 39, 40, 41, 42, 43, 44 of elastic material sandwiched between the first web section 38*a* and the third web section 45*a*, and also between the second web section 38*b* and the fourth web section 45*b*. The second sheets may be attached to each other by ultrasonic bonding, welding, adhesive, embossing, mechanical fastening, or the like. The attachment of the above-mentioned web sections and elastic strips is here described as being performed in consecutive steps but these steps are typically performed in a single step.

In order to form the crotch portion 5 (see FIG. 1*a*) with its absorbent core 17, a third continuous sheet 46 of web material is provided and forms the basis of a backsheet for the crotch portion 5. The absorbent core 17 is then laid out on the third continuous sheet 46. Also, a seventh strip 47 and an eighth strip 48 of elastic material are also laid out on the third sheet 46 of web material. The seventh strip 47 of elastic material forms the basis of the first absorbent body elastic 25 (see FIGS. 1*a* and 2), whereas the eighth strip 48 of elastic material forms the basis of the second absorbent body elastic 26.

Next, a fourth continuous sheet 49 of web material is provided and is joined to the third continuous sheet 46, suitably in a manner which is similar to that described above with reference to the first web section 38a, the second web section 38b, the third web section 45a and the fourth web section 45b. During this process, the seventh strip 47 and eighth strip 48 of elastic material, as well as the absorbent core 17, are sandwiched between said third continuous sheet 46 of web material and said fourth continuous sheet 49 of web material.

A folding procedure is next carried out so as to fold the edges of the crotch portion 5 and form the edges 36, 37 on the crotch portion 5. This folding operation is indicated in a simplified manner with the arrows 50 and 51 in FIG. 3. Similarly, folding of the front portion 3 and the back portion 4 is indicated in FIG. 3 with arrows 53, 54 in a simplified manner. This folding operation corresponds to that which is shown in FIG. 1b.

In a further manufacturing step, the web formed by means of the third sheet 46 of web material, the fourth sheet 49 of web material 49 and the absorbent core 17, is cut into individual pieces 52, each of which forms the above-mentioned crotch portion 5 which is subsequently attached to the web formed by the first and second web sections 38a, 38b and the third and fourth web sections 45a, 45b. In this regard, the crotch portion 5 is laid out at a predetermined distance so as to bridge the front portion 3 and the back portion 4 and to form the basis of the finished absorbent article. As shown in FIG. 3, a piece 52 which forms a crotch portion 5 is laid out in a transversal direction in relation to the webs forming the front portion and the back portion.

The crotch portion 5 may be attached to the chassis using any known fastening technology, such as ultrasonic bonding, welding, adhesive, embossing, mechanical fastening, or the like. In this manner, a complete chassis is formed for the article 1 in question.

In a subsequent manufacturing step, leg openings 55 are cut out of the laminated web material forming the chassis of finished absorbent articles. The cutting may be performed by any type of suitable cutting equipment (not shown in FIG. 3), such as rolling cutting using two opposite rollers.

Next, the first and fourth web sections 38b, 45b are folded to form the final product, such that the first web section 38b becomes a backsheet of the chassis and the fourth web section 45b becomes the topsheet of the chassis. This folding is shown with an arrow 56 in FIG. 3. After for example welding of side seams, the continuous assembly of products is cut into individual absorbent articles by means of cutting equipment (not shown in FIG. 3).

FIGS. 4a-e show cross-sectional views of alternative embodiments of the structure forming the back portion 4. FIG. 4a shows an embodiment in which the elastic element 23 is sandwiched between an inner side of the backsheet 33 and an inner side of the topsheet 32. The above-mentioned back elastic component 31 is also shown in FIG. 4a. Also, the backsheet 33 is folded over an outer side of said topsheet 32 so as to enclose the elastic element 23 and so as to define the edge 34. This procedure corresponds to the embodiment shown in FIG. 1b and FIG. 3.

Furthermore, FIG. 4b shows an alternative embodiment in which the elastic element 23 is enclosed and covered within a fold which is defined by the backsheet 33. Subsequently, the topsheet 32 is attached to said backsheet 33, suitably by gluing.

FIG. 4c shows a further alternative embodiment in which the elastic element 23 is sandwiched between an inner side of the backsheet 33 and an inner side of the topsheet 32, and wherein the topsheet 32 is then folded over an outer side of said backsheet 33 so as to enclose the elastic element 23. This embodiment of the absorbent article 1 is especially advantageous for having a cuff in an enhanced color formed by a colored sheet folded in an overlaying manner. The colored sheets when overlaying one another along the cuff portion creates an enhanced color of said cuff.

FIG. 4d shows a further alternative embodiment which generally corresponds to the embodiment shown in FIG. 4a, but having a back elastic component 31a which is in the form of a relatively thin strip manufactured from an elastically stretchable film. As an example, a suitable thermoplastic elastomer can be used for such a stretchable film, Furthermore, FIG. 4e shows a further alternative embodiment which generally corresponds to the embodiment shown in FIG. 4a but which shows a configuration in which the backsheet 33 is folded in a manner so that it partly encloses the elastic element 23. Consequently, this embodiment is arranged with a backsheet 33 and an elastic element 23 having other dimensions and configurations than the embodiment shown in FIG. 4a, so that the edge 34 is closer to the waist edge 8 (see also FIG. 1b) as compared with the embodiment in FIG. 4a. Even though the elastic element 23 is only enclosed partly by the folded portion of the backsheet 33, the advantages mentioned above can still be obtained, i.e. the article can be designed in a manner which is similar to regular underwear while still providing relevant protection against incontinence and also sufficient comfort and fit.

Variations of the embodiments shown in FIGS. 4d and 4e but where the topsheet and backsheet are folded as in FIG. 4b and FIG. 4c, respectively, are also possible within the scope of the invention.

FIG. 4f shows an embodiment in which the elastic element 23 is positioned at a certain distance d from the inside of the fold 33a which is defined by the backsheet 33. According to the embodiment, the distance d from the inside of the fold 33a is less than 10 mm, preferably less than 5 mm in another embodiment, and most preferably less than 3 mm in yet another embodiment, in order to obtain the advantages stated above, i.e. providing an absorbent article 1 which is similar to regular underwear while still offering sufficient protection against urine leakage.

Furthermore, FIG. 5 shows a cross-sectional view of an embodiment involving the crotch section 5 and in particular showing the second absorbent body elastic 26 (see also FIG. 1a and FIG. 2). According to this embodiment, the crotch portion comprising a further web material 58 which is folded over the laminate which is defined by the topsheet 32 and the backsheet 33. In this manner, the second absorbent body elastic 26 is enclosed. According to a further embodiment, the crotch portion 5 can be equipped with so-called standing gathers comprising elastic elements 57 which are enclosed by a section of the further web material 58 which is attached to the topsheet 32 by means of adhesive 59 or another suitable fastening means. A similar arrangement can be made as regards the first absorbent body elastic 25 (see FIG. 1a and FIG. 2).

The invention is not limited to the embodiment but can be varied within the scope of the appended claims. For example, the principles of the present invention are equally applicable to any type of hygienic absorbent article. Such articles include various types of incontinence liners and pads, and also sanitary napkins, menstrual pads, panty liners or similar products which are worn inside a supporting panty or which a holder. Such articles also include baby diapers with tape fasteners, pant diapers, training pants, belted diapers or similar disposable absorbent garments.

Reference signs mentioned in the claims should not be seen as limiting the extent of the matter protected by the claims, and their sole function is to make claims easier to understand.

As will be realised, the disclosure is capable of modification in various obvious respects, all without departing from the scope of the appended claims. Accordingly, the drawings and the description thereto are to be regarded as illustrative in nature, and not restrictive. It should be understood that the present absorbent articles and its components and methods are not intended to be limited to the particular forms disclosed. Rather, they are intended to include all modifications, equivalents, and alternatives falling within the scope of the claims. They are further intended to include embodiments that may be formed by combining features from the disclosed embodiments, and variants thereof.

The invention claimed is:

1. An absorbent article having a longitudinal direction, a transverse direction and a thickness direction and comprising a topsheet, a backsheet and an absorbent core, and also having, in the longitudinal direction, a front portion, a back portion and a crotch portion between the front portion and the back portion, wherein the front portion defines a front waist edge and a front leg edge, the back portion defines a back waist edge and a back leg edge, and the crotch portion defines two crotch edges and
   wherein a first elastic element extends along the front waist edge, a second elastic element extends along the front leg edge and a third and a fourth elastic element each extend along one of the crotch edges, wherein the second elastic element is separate from the third and fourth elastic elements,
   wherein at least one of the topsheet and backsheet and an additional sheet is folded along said front waist edge, the front leg edge and the two crotch edges so as to enclose at least a part of each of the first, second, third, and fourth elastic elements, wherein the second elastic element is enclosed in a separate fold from the folds enclosing the third and fourth elastic elements.

2. The absorbent article according to claim 1, wherein at least one of said the topsheet and the backsheet and the additional sheet is folded along the back leg edge.

3. The absorbent article according to claim 1, wherein at least one of said first, second, third, and fourth elastic elements is sandwiched between an inner side of said backsheet and an inner side of said topsheet, and wherein said backsheet is folded over an outer side of said topsheet.

4. The absorbent article according to claim 1, wherein at least one of said first, second, third, and fourth elastic elements is sandwiched between an inner side of said backsheet and an inner side of said topsheet, and wherein said topsheet is folded over an outer side of said backsheet.

5. The absorbent article according to claim 4, wherein a distance (d) from the inside of said fold and said at least one elastic element is less than 10 mm.

6. The absorbent article according to claim 5, wherein the distance (d) is less than 5 mm.

7. The absorbent article according to claim 5, wherein the distance (d) is less than 3 mm.

8. The absorbent article according to claim 1, wherein at least one of said first, second, third, and fourth elastic elements is enclosed within a fold defined by said backsheet, and wherein said topsheet is attached to said backsheet.

9. The absorbent article according to claim 1, wherein at least one of said first, second, third, and fourth elastic elements is enclosed within a fold defined by said topsheet, and wherein said topsheet is attached to said backsheet.

10. The absorbent article according to claim 1, wherein the additional sheet is a web material, said crotch portion comprises the web material which is folded over said two crotch edges.

11. The absorbent article according to claim 10, wherein at least one of said the topsheet and the backsheet is folded along the front leg edge.

12. The absorbent article according to claim 1, wherein said first elastic element defines an elastic waist component, said second elastic component defines an elastic leg component, and said third elastic component and said fourth elastic component define elastic absorbent body components.

13. The absorbent article according to claim 12, wherein said first, second, third, and fourth elastic elements comprise elastic threads.

14. The absorbent article according to claim 1, wherein the absorbent article is an incontinence article.

15. The absorbent article according to claim 1, wherein the absorbent article further comprises a cuff in color, wherein the cuff is formed by a colored sheet folded in an overlaying manner.

16. A method for manufacturing an absorbent article having a longitudinal direction, a transverse direction and a thickness direction, said method comprising:
   providing a topsheet a backsheet and an absorbent core;
   forming, in the longitudinal direction of the article, a front portion, a back portion and a crotch portion between the front portion and the back portion, wherein the front portion defines a front waist edge and a front leg edge, the back portion defines a back waist edge and a back leg edge, and the crotch portion defines two crotch edges; and
   providing a first elastic element extending along the front waist edge, a second elastic element extending along the front leg edge and a third and a fourth elastic element each extending along one of the crotch edges, wherein the second elastic element is separate from the third and fourth elastic elements, and
   folding at least one of the topsheet and backsheet or an additional sheet along said front waist edge, the front leg edge and the two crotch edges so as to enclose at least a part of each of the first, second, third, and fourth elastic elements, wherein the second elastic element is enclosed in a separate fold from the folds enclosing the third and fourth elastic elements.

17. The method according to claim 16, further comprising:
   sandwiching at least one of said first, second, third, and fourth elastic elements between an inner side of said backsheet and an inner side of said topsheet; and
   folding said backsheet over an outer side of said topsheet.

18. The method according to claim 16, further comprising:
   sandwiching at least one of said first, second, third, and fourth elastic elements between an inner side of said backsheet and an inner side of said topsheet; and
   folding said topsheet over an outer side of said backsheet.

19. The method according to claim 16, further comprising:
   enclosing at least one of said first, second, third, and fourth elastic elements within a fold defined by said backsheet; and attaching said topsheet to said backsheet.

20. The method according to claim 16, further comprising:
- enclosing at least one of said first, second, third, and fourth elastic elements within a fold defined by said topsheet, and attaching said topsheet to said backsheet.

21. The method according to claim 16, further comprising:
- providing said crotch portion with the additional sheet, the additional sheet being a web material, and
- folding said web material over said crotch edges.

* * * * *